(12) United States Patent
Bakker

(10) Patent No.: US 8,106,044 B2
(45) Date of Patent: *Jan. 31, 2012

(54) 8-{4-[3-(5-FLUORO-1H-INDOL-3-YL)-PROPYL]-PIPERAZIN-1-YL}-2-METHYL-4H-BENZO[1,4]OXAZIN-3-ONE MESYLATE WITH HIGH AFFINITY FOR THE DOPAMINE $D_2$ RECEPTOR AND THE SEROTONIN REUPTAKE SITE

(75) Inventor: Cornelis Bakker, Weesp (NL)

(73) Assignee: Solvay Pharmaceuticals B.V., Weesp (NL)

( * ) Notice: Subject to any disclaimer, the term of this patent is extended or adjusted under 35 U.S.C. 154(b) by 37 days.

This patent is subject to a terminal disclaimer.

(21) Appl. No.: 11/134,455

(22) Filed: May 23, 2005

(65) Prior Publication Data

US 2005/0209228 A1  Sep. 22, 2005

Related U.S. Application Data

(62) Division of application No. 10/432,225, filed as application No. PCT/EP02/01795 on Feb. 19, 2002, now Pat. No. 6,958,396.

(30) Foreign Application Priority Data

Feb. 21, 2001  (EP) .................................... 01200610

(51) Int. Cl.
*A61K 31/538* (2006.01)
*C07D 413/12* (2006.01)
(52) U.S. Cl. ..................................... 514/230.5; 544/105
(58) Field of Classification Search .................. 544/105; 514/230.5
See application file for complete search history.

(56) References Cited

U.S. PATENT DOCUMENTS

| | | | |
|---|---|---|---|
| 5,002,948 A | 3/1991 | Perregaard et al. |
| 5,242,925 A | 9/1993 | Boettcher et al. |
| 5,314,896 A | 5/1994 | Caprathe et al. |
| 5,532,241 A | 7/1996 | Böttcher et al. |
| 5,576,321 A | 11/1996 | Krushinski, Jr. et al. |
| 5,693,655 A | 12/1997 | Böttcher et al. |
| 6,214,829 B1 | 4/2001 | Feenstra et al. |
| 6,251,908 B1 | 6/2001 | Böttcher et al. |
| 6,262,087 B1 | 7/2001 | Perregaard et al. |
| 6,352,988 B2 | 3/2002 | Perregaard et al. |
| 6,391,896 B1 | 5/2002 | Van Hes et al. |
| 6,552,044 B2 | 4/2003 | Perregaard et al. |
| 6,828,325 B2 | 12/2004 | Feenstra et al. |
| 6,958,396 B2 * | 10/2005 | Bakker ........................ 544/105 |
| 7,067,513 B1 * | 6/2006 | Van Hes et al. ............. 514/224.2 |
| 2001/0020095 A1 | 9/2001 | Perregaard et al. |
| 2001/0021777 A1 | 9/2001 | Perregaard et al. |
| 2004/0024207 A1 * | 2/2004 | Bakker ........................ 544/105 |

FOREIGN PATENT DOCUMENTS

| | | |
|---|---|---|
| DE | 41 27 849 A1 | 2/1993 |
| DE | 43 33 254 A1 | 4/1995 |
| DE | 44 14 113 A1 | 10/1995 |
| DE | 197 30 989 A1 | 1/1999 |
| EP | 0 376 607 A1 | 7/1990 |
| EP | 0 722 941 A2 | 7/1996 |
| GB | 1 075 156 | 7/1967 |
| HU | 218 935 B | 10/1995 |
| WO | WO 97/17343 | 5/1997 |
| WO | WO 98/28293 | 7/1998 |
| WO | WO 99/03855 | 1/1999 |
| WO | WO 99/05140 | 2/1999 |
| WO | WO 99/67237 | 12/1999 |
| WO | WO 01/14330 A2 | 3/2001 |
| WO | WO 03/068207 | 8/2003 |

OTHER PUBLICATIONS

Racemic mixture, from Wikipedia, the free encyclopedia,1 page,retrieved from the Internet Feb. 15, 2011 at http://en.wikipedia.org/wiki/Racemic_mixture.*
Robichaud et al.,"Recent Advances in Selective Serotonin Receptor Modulation," *Ann. Rep. Med. Chem.* 35:11-21 (2000).
Tenbrink et al., "Recent Advances in Dopamine $D_3$ and $D_4$ Receptor Ligands and Pharmacology," *Ann. Rep. Med. Chem.* 29:43-51 (1994).

* cited by examiner

*Primary Examiner* — Emily Bernhardt
(74) *Attorney, Agent, or Firm* — Finnegan, Henderson, Farabow, Garrett & Dunner LLP

(57) ABSTRACT

The invention relates to the novel mesylate of a phenylpiperazine derivative of the formula (I). This salt has a favorable properties as compared with the free base of this compound.

8 Claims, No Drawings

8-{4-[3-(5-FLUORO-1H-INDOL-3-YL)-PROPYL]-PIPERAZIN-1-YL}-2-METHYL-4H-BENZO[1,4]OXAZIN-3-ONE MESYLATE WITH HIGH AFFINITY FOR THE DOPAMINE $D_2$ RECEPTOR AND THE SEROTONIN REUPTAKE SITE

This is a divisional application of U.S. application Ser. No. 10/432,225, filed May 22, 2003, which issued as U.S. Pat. No. 6,958,396, on Oct. 25, 2005, which is a §371 of PCT/EP 0201795, filed Feb. 19, 2002, which claims the benefit of priority of EP 01200610.2, filed Feb. 21, 2001, all of which are incorprated herein by reference.

The invention relates to the novel phenylpiperazine derivative of the formula (I):

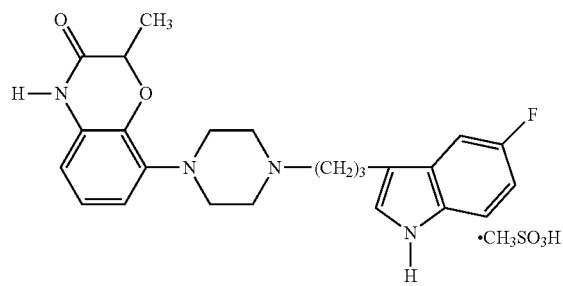

Patent application No. PCT/EP 00/08090 (not yet published) relates a group of novel phenyl piperazines. The compounds of that group show high affinity for both the dopamine $D_2$ receptor and the serotonin reuptake site. This combination is useful for the treatment of schizophrenia and other psychotic disorders which enables a more complete treatment of all disease symptoms (e.g. positive symptoms and negative symptoms).

The compounds show activity as antagonists at dopamine $D_2$ receptors as they potentially antagonize apomorphine-induced climbing behaviour in mice. The compounds also show activity as inhibitors of serotonin reuptake, as they potentiate 5-HTP induced behaviour in mice.

The compounds are active in therapeutic models sensitive to clinically relevant antipsychotics (e.g. the conditioned avoidance response; Van der Heyden & Bradford, Behav. Brain Res., 1988, 31:61-67) and antidepressants or anxiolytics (e.g. suppression of stress-induced vocalization; van der Poel et al., Psychopharmacology, 1989, 97:147-148).

In contrast to clinically relevant dopamine $D_2$ receptor antagonists the described compounds have a low propensity to induce catalepsy in rodents and as such are likely to induce less extrapyramidal side effects than existing antipsychotic agents.

The inhibitory activity of serotonin reuptake inherent in these compounds may be responsible for the therapeutic effects observed in behavioural models sensitive to either antidepressants or anxiolytics.

The compounds can be used for the treatment of affections or diseases of the central nervous system caused by disturbances in either the dopaminergic or serotonergic systems, for example: aggression, anxiety disorders, autism, vertigo, depression, disturbances of cognition or memory, Parkinson's disease, and in particular schizophrenia and other psychotic disorders.

It has now been found that the mesylate of the above formula has particularly favourable properties in comparison with the free base (i.e. compound no. 89 of EP 99202710.2).

This mesylate compound is much better soluable in water than the free base resulting in a good bio-availability.

The compound has a centre of chirality; both the racemic mixture and the individual enantiomers belong to the invention.

The compound can be brought into forms suitable for administration by means of suitable processes using auxiliary substances such as liquid and solid carrier materials.

The free base of compounds in general can be prepared as described in International Publication No. WO 01/14330 A2. The compounds of the present invention can be prepared by reaction of a compound of formula

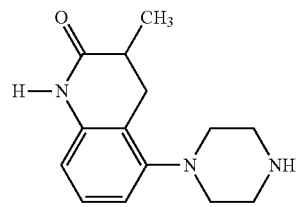

under basic conditions with a compound of formula

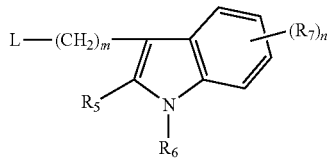

in which L is a leaving group such as a halogen atom or a mesylate group, m is 3, $R_5$ and $R_6$ are both hydrogen, and $R_7$ is a fluorine on the 5-position of the indole ring while n is 1.

For example, a mixture of the piperazine of formula (II) (3.36 g, 13.6 mmol), the 5-fluoro indole-mesylate of formula (III) (4.1 g, 15.1 mmol), triethylamine (2 ml) and a catalytic amount of KI in $CH_3CN$ (100 ml) was heated under reflux for 18 hours after which the reaction mixture was concentrated in vacuo and purified by chromatography ($SiO_2$, dichloromethane/methanol/ammonium hydroxide =92/7.5/0.5).

Yield of the free base of the compound was 58%, $[\alpha]_D^{25}=-24°$ (methanol).

One enantiomer of the starting compound of formula (II) can be prepared according to the following scheme:

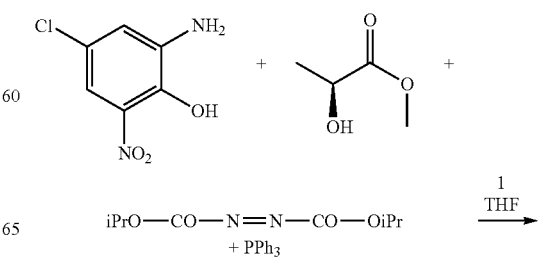

-continued

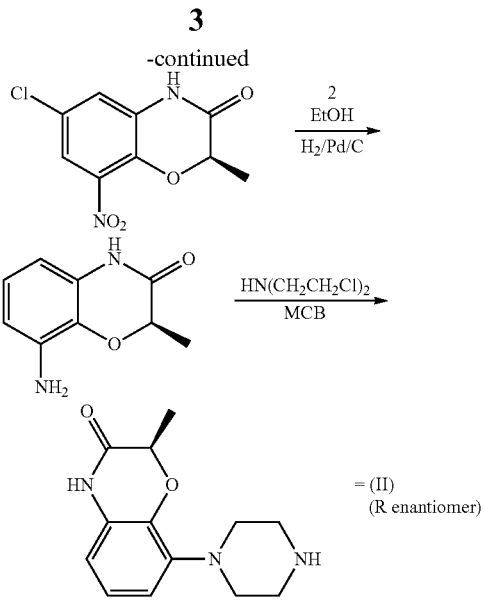

The free base can be converted into the mesylate according to processes known per se for salt formation.

The invention is illustrated by means of the following Example.

EXAMPLE 2.0 g (4.7 mmol) of the free base obtainable as described in EP 99202710.2 (compound no. 89) is suspended in 40 ml of methanol. The suspension is warmed to 60° C., and a solution of 0.45 g (4.7 mmol) of methanesulfonic acid in 10 ml of methanol is added in about two minutes. A clear solution is obtained. After stirring for 5 minutes at 60° C. the crystallization begins. The solution is cooled slowly in 60 minutes to 20° C., and stirred at that temperature for 30 minutes. Further cooling to 0 °C. in 60 minutes and stirring for 90 minutes is carried out. The solid material is isolated by means of filtration, washed with 5 ml of methanol and dried during a night at 50° C. under reduced pressure. Yield 2.17 g (88%) of white coloured mesylate.

The invention claimed is:

1. A method of preparing a pharmaceutical composition comprising combining an effective amount of at least one compound of the formula:

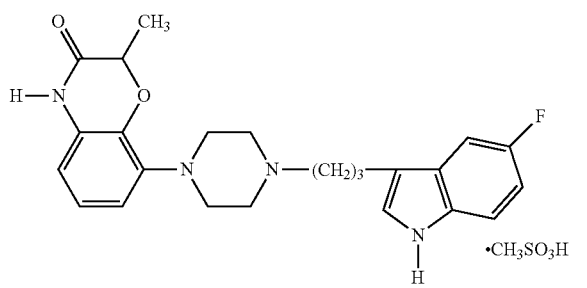

with at least one auxiliary substance.

2. The method of preparing a pharmaceutical composition as set forth in claim 1, wherein at least one compound comprises the R enantiomer.

3. The method of preparing a pharmaceutical composition as set forth in claim 1, wherein at least one compound comprises the S enantiomer.

4. The method of preparing a pharmaceutical composition as set forth in claim 1, wherein the composition comprises both the R enantiomer and the S enantiomer of at least one compound.

5. The method of preparing a pharmaceutical composition as set forth in claim 1, wherein at least one auxiliary substance comprises a solid carrier.

6. The method of preparing a pharmaceutical composition as set forth in claim 1, wherein the at least one auxiliary substance comprises a liquid carrier.

7. A compound of the formula:

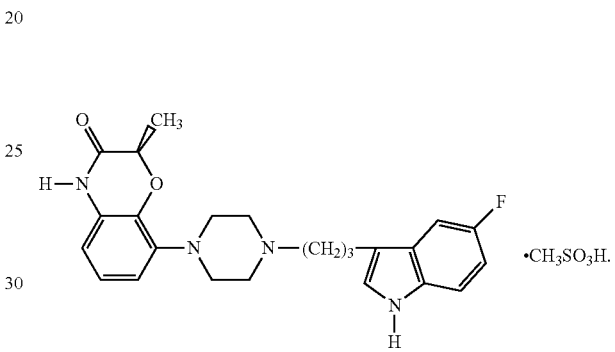

8. A compound of the formula:

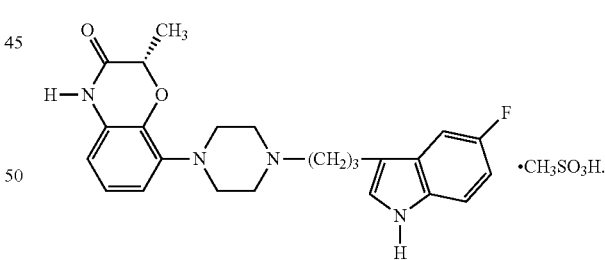

* * * * *

UNITED STATES PATENT AND TRADEMARK OFFICE
CERTIFICATE OF CORRECTION

| | | |
|---|---|---|
| PATENT NO. | : 8,106,044 B2 | Page 1 of 1 |
| APPLICATION NO. | : 11/134455 | |
| DATED | : January 31, 2012 | |
| INVENTOR(S) | : Bakker | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 114 days.

Signed and Sealed this
Twenty-fourth Day of July, 2012

David J. Kappos
*Director of the United States Patent and Trademark Office*